United States Patent [19]

Gardin et al.

[11] Patent Number: 4,913,159
[45] Date of Patent: Apr. 3, 1990

[54] METHOD FOR DETERMINING BLOOD FLOW THROUGH A NARROWED ORIFICE USING COLOR DOPPLER ECHOCARDIOGRAPHY

[75] Inventors: Julius M. Gardin, Long Beach, Calif.; Toshio Ogawa, Tokyo, Japan; Toshinori Utsunomiya, Santa Ana; Hoang A. Tang, Orange, both of Calif.

[73] Assignees: Hitachi Medial Corp., Tokyo, Japan; The Regents of the University of California, Oakland, Calif.

[21] Appl. No.: 325,562

[22] Filed: Mar. 17, 1989

[51] Int. Cl.$^4$ .............................................. A61B 8/00
[52] U.S. Cl. ............................... 128/661.1; 73/861.25
[58] Field of Search ................... 128/661.1; 73/861.25

[56] References Cited

U.S. PATENT DOCUMENTS 4,790,322 12/1988 Iinuma .............................. 128/661.1

OTHER PUBLICATIONS

H. Rouse, *Elementary Mechanics of Fluids*, John Wiley & Sons, Inc., New York, 1946, pp. 87–102.
K. Miyatake, M.D., et al., "Semiquantitative Grading of Severity of Mitral Regurgitation by Real-Time Two-Dimensional Doppler Flow Imaging Technique," *Journal of the American College of Cardiology*, vol. 7, No. 1, Jan. 1986, pp. 82–88.
Brian Hoit, et al., "Acceleration of Blood Flow Proximal to the Point of Systolic Anterior Motion in Hypertrophic Obstructive Cardiomyopathy: Demonstration of the Venturi Effect by Color Flow Mapping Doppler," Circulation, vol. 74, Supp II, No. 4, Oct. 1986, p. II-130.
Ann F. Bolger, et al., "Relationship of Color Doppler Jet Area to Flow Volume: Reliability and Limitations," Circulation, Abstracts of the 59th Scientific Sessions, vol. 74, Supp II, No. 4, Oct. 1986, p. II-216.
David J. Sahn, et al., "Factors Affecting Jet Visualization by Color Flow Mapping Doppler Echo: In Vitro Studies," Circulation, Abstracts of the 59th Scientific Sessions, vol. 74, Supp II, No. 4, Oct. 1986, p. II-271.
Frederick Helmcke, M.D., et al., "Color Doppler Assessment of Mitral Regurgitation with Orthogonal Planes," Circulation, vol. 75, No. 1, Jan. 1987, pp. 175–183.

(List continued on next page.)

*Primary Examiner*—Francis Jaworski
*Attorney, Agent, or Firm*—Knobbe, Martens, Olson & Bear

[57] ABSTRACT

A multi-gated pulsed wave color Doppler imaging system is used to provide accurate non-invasive measurements of liquid flow through a narrowed orifice by using the color Doppler to first measure the velocity of flow along an axis perpendicular to the orifice to provide a first image of the liquid velocity. The first image includes a two-color interface at locations in the image representing locations where the liquid velocity is equal to the aliasing velocity of the color Doppler imaging system. The distance from the two-color interface to the center of the orifice is measured and saved. A second image is obtained along an axis perpendicular to the first axis to represent the flow of liquid to the orifice from the perimeter of the orifice. The distance from a two-color interface to the center of the orifice in the second image is measured. The two measured dimensions are used to model a hemi-ellipsoidal surface proximal to the orifice wherein all points on the surface have the same isovelocity. The surface area is multiplied by the aliasing velocity to obtain the volume fluid flow rate through the orifice. A third image can also be obtained along a third axis perpendicular to the first and second axes and used to model an alternative hemi-ellipsoidal isovelocity surface. In a further alternative, a single image can be used to model a panshaped isovelocity surface.

7 Claims, 13 Drawing Sheets

OTHER PUBLICATIONS

Michael Jones, M.D., et al., "Variability of Color Flow Mapping Doppler Imaging of Regurgitant Jets in an Animal Model of Mitral Insufficiency," *Journal of the American College of Cardiology*, Abstracts, vol. 9, No. 2, Feb. 1987, p. 64A.

Ann F. Bolger, M.D., et al., "Quantification of Jet Energy by Computer Analysis of Color Doppler Images," *Journal of the American College of Cardiology*, Abstracts, vol. 9, No. 2, Feb. 1987, p. 65A.

Gilbert J. Perry, M.D., et al., "Evaluation of Aortic Insufficiency by Doppler Color Flow Mapping," *Journal of the American College of Cardiology*, vol. 9, No. 4, Apr. 1987, pp. 952-959.

Iain A. Simpson, M.D., et al., "Determinants of Color Flow Doppler Imaging of Regurgitant Flows in a Physiological In-Vitro Model of Mitral Insufficiency Evaluated by Digital Computer Analysis of Color Coded Velocities," *Journal of the American College of Cardiology*, Feb. 1988, vol. 11, No. 2, p. 19A.

N. Morichika, et al., "Assessment of Suction Signal Imaging by Color Doppler Echocardiography in Patients with Aortic Regurgitation," Japan Society of *Ultrasonics in Medicine Proceedings*, Abstract, vol. 52, Jun. 1988, pp. 335-336.

G. S. Bargiggia, et al., "Quantitative Assessment of Mitral Regurgitation by Color Doppler Analysis of Flow Convergence Region: Usefulness of Continuity Equation," *Proceedings of the Sixth International Congress on Cardiac Doppler*, Abstract, Rome, Italy, Jun. 23-25, 1988, p. 140.

Toshinori Utsunomiya, et al., "Effect of Machine Parameters on Variance Image Display in Doppler Color Flow Mapping", *Circulation*, Abstracts of the 61st Scientific Sessions, vol. 78, Supp. II, No. 4, Oct. 1988, p. II-12.

J. Geoffrey Stevenson, "Critical Importance of Gain, Pulse Repetition Frequency and Carrier Frequency Upon Apparent 2d Color Doppler Jet Size," *Circulation*, Abstracts of the 61st Scientific Sessions, vol. 78, Supp II, No. 4, Oct. 1988, p. II-12.

James D. Thomas, et al., "Quantification of Jet Flow by Momentum Analysis: An In Vitro Color Doppler Study," *Circulation*, Abstracts of the 61st Scientific Sessions, vol. 78, Supp II, No. 4, Oct. 1988, p. II-609.

G. S. Bargiggia, et al., "Color Flow Doppler Quantitation of Regurgitatn Flow Rate Using the Flow Convergence Region Proximal to the Orifice of a Regurgitant Jet," *Circulation*, Abstracts of the 61st Scientific Sessions, vol. 78, No. 4, Supp II, Oct. 1988, p. II-609.

David J. Sahn, M.D., "Instrumentation and Physical Factors Related to Visualization of Stenotic and Regurgitant Jets by Doppler Color Flow Mapping," *Journal of the American College of Cardiology*, vol. 12, No. 5, Nov. 1988, pp. 1354-1365.

Valdir Moises, M.D.,. et al., "Consistency of Color Flow Doppler Estimation of Regurgitant Flow Rate Across Varying Size Orifices and Multiple Orifice Communications Using Flow Convergence Concepts: Studies in an In-Vitro Model," *Jour. of the Am. Coll. of Cardiology*, vol. 13, No. 2, Feb. 1989, p. 22A.

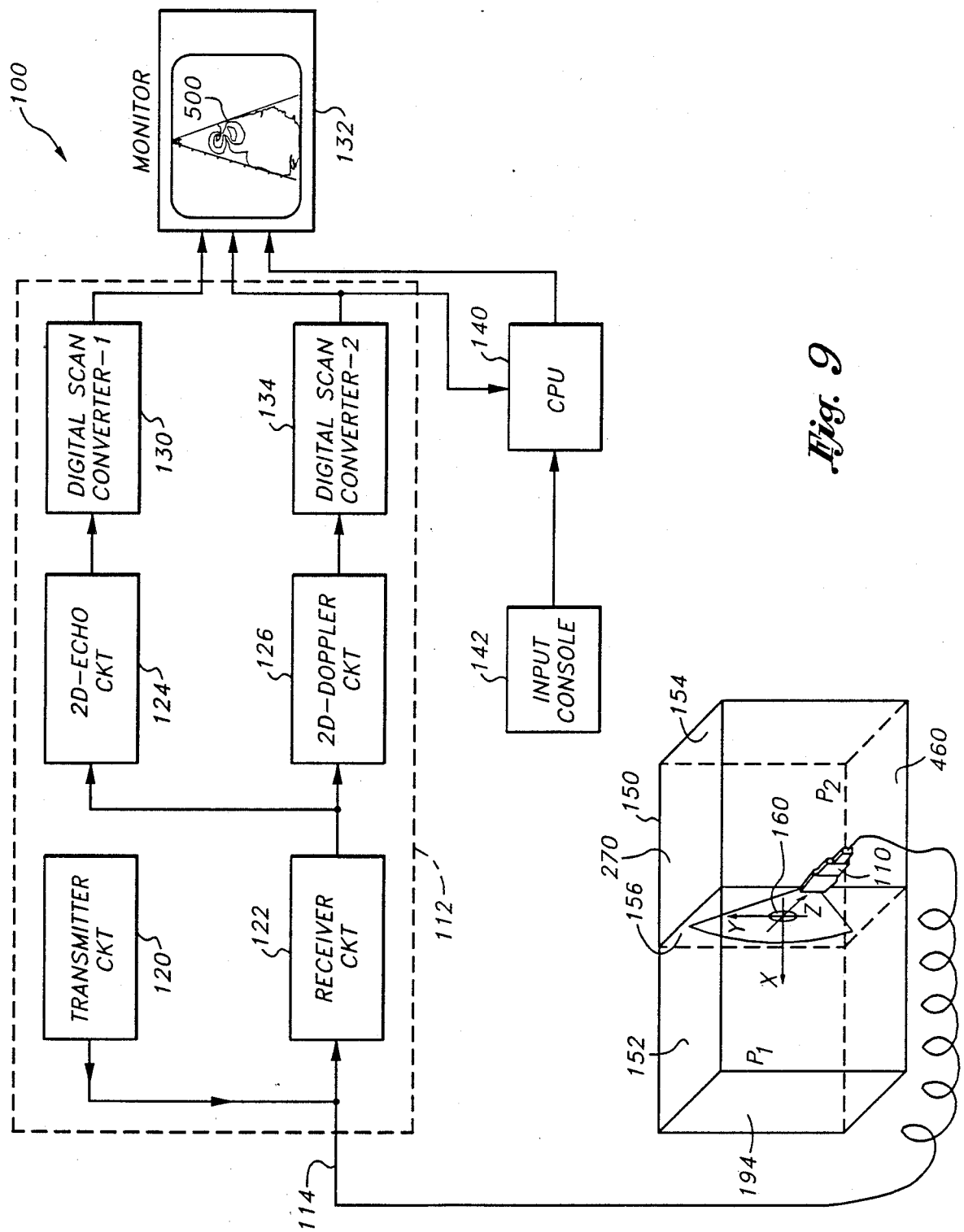

METHOD FOR DETERMINING BLOOD FLOW THROUGH A NARROWED ORIFICE USING COLOR DOPPLER ECHOCARDIOGRAPHY

BACKGROUND OF THE INVENTION

1. Field of the Invention

The present invention is in the field of noninvasive cardiac monitoring, and, more particularly, in the field of color Doppler blood flow imaging wherein the velocity of blood flow in a vessel or through an orifice is represented by color images on a display with different colors representing different velocities and different directions.

2. Description of the Related Art

Color flow mapping using the Doppler effect is a method for noninvasively imaging blood flow through the heart and other vessels by displaying flow data on a twodimensional echocardiographic image such as an image on a color CRT monitor, or the like.

Color flow mapping operates by directing an ultrasonic signal toward the heart from an ultrasonic transducer positioned outside the patient and using a sensing transducer to monitor the return echo generated by the signal. As is well known in the field of echocardiography, the return signal will arrive at a sensing transducer at a time that is determined by the distance that the signal has travelled from the generating transducer to a sound reflecting material and back to the sensing transducer. The signal will have an intensity that is determined by the structural characteristics of the reflecting material. These characteristics of the sensed echo have been used in conventional echocardiography to map the physical structure of the heart and other related structures of the patient. This technique uses color encoding to display velocities from multiple sample volumes using multi-gated pulse Doppler techniques.

Color Doppler echocardiography further monitors the frequency of the sensed echo to determine additional information. It has been known that an echo from a moving object is shifted in frequency with respect to a transmitted signal in accordance with the velocity of the moving object and the direction in which the object is moving with respect to the sensing transducer. This so-called Doppler effect has been used, for example, in radar, sonar, and the like, to monitor moving objects and determine their velocities. In color Doppler echocardiography, the Doppler effect is used to determine blood flow characteristics, and, in particular, is used to identify constrictions in vessels, regurgitation (i.e., leaks or back flow) in heart valves, leaks between the chambers of the heart, and the like.

The operation of color Doppler echocardiography is well understood in the medical field and is described, for example, in Joseph Kisslo, et al., "DOPPLER COLOR FLOW IMAGING," Churchill Livingston, Inc., New York, 1988 (ISBN 0-443-08563-3), and in "COLOR ATLAS of Real-Time Two-Dimensional Doppler Echocardiography," Second Edition, Ryozo Omoto, M. D., Editor, Shindan-to-Chiryo Co., Ltd., Tokyo, 1987 (ISBN 0-8121-1116-8). Additional background information regarding color Doppler echocardiography can be found in the two references.

A number of color Doppler imaging systems are commercially available for performing color Doppler echocardiography. One such system is the Model EUB-151 Ultrasound Sector Scanner with Digital Scan Converter available from Hitachi Medical Corporation of Tokyo, Japan, available in the United States as the Model CVC-151 from Biosound. Basically, such systems operate by using a probe having an ultrasonic transducer that generates an ultrasonic signal as a series of pulses and a sensing transducer to sense the return echoes. The probe is positioned to direct the ultrasonic signal pulses toward a region of interest in the patient (e.g., toward the heart). The probe includes circuitry to cause the ultrasonic signal pulses to be scanned in a fan-like pattern so that the ultrasonic signal pulses pass through a planar area of the region of interest. By measuring the time of arrival of the return pulses from the region of interest, a two-dimensional representation of the structural characteristics of the region of interest can be generated. In addition, as discussed above, the return signal pulses are shifted in frequency when they are reflected from moving material in the region of interest. The color Doppler imaging system includes a processor and other suitable electronic hardware and software to measure the frequency shifts of the return signal pulses and to correlate the frequency shifts with the times of arrival of the return signal pulses to generate a two dimensional representation of the flow in the region of interest. The two-dimensional representation is displayed in color on a display monitor (e.g., a color CRT) with different colors representing different velocities and directions of movement in the region of interest. Such movement is generally the flow of blood through the heart and other vessels.

In a typical color Doppler imaging system, two distinct ranges of colors are used to indicate flow direction and velocity. For example, in one exemplary system, a range of blue colors from light blue to dark blue are used to indicate flow toward the probe and a range of red colors are used to indicate flow away from the probe. Other colors may of course be used, and some imaging systems allow the operator to select the colors used to represent flow velocities and directions and to select the range of velocities represented by a particular range of colors.

It has been found that in color Doppler imaging systems using ultrasonic pulses, such as described above, a phenomenon referred to as "aliasing" occurs. Since the pulsed operation of a color Doppler imaging system is basically operating in a sampling mode, the aliasing phenomenon occurs because of the inability of the system to faithfully record velocities, as well as the direction of flow, above a certain velocity (i.e., one-half the Nyquist limit) for a given depth setting ("range") and ultrasound transducer frequency. When aliasing occurs, the color displayed on the display monitor will appear as the color associated with a high velocity in the opposite direction. For example, in an imaging system where bright blue represents the maximum velocity toward the probe and bright red represents maximum velocity away from the probe, when the blood flow towards the probe exceeds the maximum velocity, the displayed color will switch from bright blue to bright red. Since a skilled operator of the imaging system will know that the blood flow cannot make an abrupt transition in direction at the maximum velocities indicated, the operator will know that the transition from bright blue to bright red on the display is a distinct indication that the blood flow at a particular location is moving at a rate referred to as the aliasing velocity. Since the operator can adjust the ranges of velocities that can be represented by the red and blue color ranges, the operator will know that the blood flow at the red/blue interface has a velocity equal to the maximum velocity of the range.

Heretofore, the color Doppler imaging systems have been used to identify imperfections in the cardiac system as indicated by blood flow between chambers of the heart caused by openings in the chamber walls, regurgitation of blood caused by incomplete closure of a heart valve, disturbed flow caused by obstructions, and the like. Such imperfections are identifiable qualitatively by observing the color patterns on the display monitor. However, quantitative measurement capability has not been perfected to enable a clinician to determine noninvasively the quantity of blood flowing through a leak or through an obstruction in a vessel or valve so that the clinician can determine whether the defect requires immediate surgical intervention or medication and so that the clinician can make comparisons over a period of time to determine whether the defect is becoming worse.

There have been attempts to make quantitative measurements of blood flow distal to an orifice such as an orifice in the chamber wall between two chambers of a patient's heart. Such attempts have generally not been very successful because of a number of machine factors such as the system gain of the imaging system, the transmit power, the frame rate, and the like, which can vary from measurement to measurement, thus preventing accurate quantification of the measured flow.

It has recently been suggested that the red/blue color interface representing blood flow proximal to an orifice can be used to provide quantitative measurements of blood flow in patients having mitral regurgitation. See, for example, G. S. Bargiggia, et al., "QUANTITATIVE ASSESSMENT OF MITRAL REGURGITATION BY COLOR DOPPLER ANALYSIS OF FLOW CONVERGENCE REGION: USEFULNESS OF CONTINUITY EQUATION," *Sixth International Congress on Echocardiography*, Rome, Italy, June 23-25, 1988, page 140. As discussed above, the red/blue color interface represents the aliasing velocity which corresponds to the limit of the range of the velocity that can be represented by a distinct color in a given direction. Thus, all pixels on the displayed image at the red/blue color interface have the same aliasing velocity. The red/blue color interface is thus referred to as the isovelocity line. Bargiggia, et al., suggest that the flow velocity increases as the flow stream lines converge toward an orifice (i.e., a partially open mitral valve), and that symmetry requires that all velocities be the same at the same radial distance from the orifice. Bargiggia, et al., then suggest that the isovelocity line can be used to model a hemispherical surface at a radial distance r from the orifice wherein the velocities are the same. By multiplying the surface area of the surface by the velocity, Bargiggia, et al., proposed to calculate the flow rate.

Applicants have compared the flow rates calculated using the Bargiggia, et al., method with known flow rates in experiments wherein the actual flow rate can be accurately determined by empirical methods. As a result of the experiments, it has been determined that the Bargiggia, et al., method is not sufficiently accurate to be used for quantitative measurements of blood flow rate. Thus, a need continues to exist for an accurate method of using color Doppler imaging techniques to quantify flow rates through an orifice.

SUMMARY OF THE PRESENT INVENTION

One aspect of the present invention is a method for estimating a volume of flow of a liquid across an orifice at a wall which separates a first chamber and a second chamber in an object. The method comprises the step of transmitting ultrasonic beams to the first chamber which is proximal to the orifice and measuring a first flow velocity distribution within a first plane in the first chamber using the Doppler shift of ultrasonic waves reflected from particles in the flow. The first flow velocity distribution is displayed as a color image on a display monitor or the like. The transmitting step is repeated to generate a second flow velocity distribution image representing the flow in a second plane in the chamber orthogonal to the first plane. The method further includes the step of describing an isovelocity surface on which a plurality of isovelocity points indicate a specified velocity on the flow velocity distribution of the liquid. The isovelocity surface is described by an elliptical model. The method further includes the step of estimating the volume of the flow by calculating an area of the isovelocity surface of the elliptical model and multiplying the area by the specified velocity.

Preferably, the elliptical model is a surface of revolution, generated by rotating an ellipse defined by $$X^2/A^2 + Y^2/B^2 = 1,$$

wherein the axis of revolution is the X-axis which corresponds to an axis perpendicular to the wall separating the first and second chambers and penetrating the center of the orifice, and A and B are found as described below.

The step of describing the model includes the steps of determining an X-intercept A of the ellipse by locating a first point on the X-axis of the first flow velocity distribution image at which the flow velocity is the specified velocity within the flow velocity distribution; and determining a Y-intercept B of the ellipse by locating a second point on the Y-axis of the second flow velocity distribution image at which the flow velocity is the specified velocity.

In this aspect of the method, the first flow velocity distribution is obtained through an array ultrasonic transducer, the center of the transducer being positioned on the X-axis and the array direction thereof being oriented so that ultrasonic signals scan in a first plane in which the X-axis lies (e.g., the X-Y plane). The second flow velocity distribution is obtained through the array ultrasonic transducer when the array direction is positioned so that the ultrasonic signals scan in a second plane perpendicular to the first plane and perpendicular to the X-axis (e.g., in a plane parallel to the Y-Z plane).

In an alternative technique, the method of the present invention is used to describe an elliptical model of an isovelocity surface comprising points {X, Y, Z} in an X, Y, Z coordinate system having an origin at the center of the orifice with the X-axis being coincident to the flow direction through the orifice, and the Y-axis and the Z-axis each being mutually perpendicular and perpendicular to the X-axis. Each of the points {X, Y, Z} on the isovelocity surface satisfies the relationship $$X^2/A^2 + Y^2/B^2 + Z^2/C^2 = 1,$$

The isovelocity surface is hemi-ellipsoidal in that it comprises only the points on the surface on one side of a Y-Z plane through the origin (e.g., the X values of all the points are all positive in accordance with the convention described herein). The step of describing the model includes the steps of determining an X-intercept A using a first flow distribution lying along the X-axis in an X-Y plane; determining a Y-intercept B using a second flow velocity distribution lying in the direction of the Y-axis in a plane parallel to the Y-Z plane; and determining a Z-intercept B using a third flow velocity distribution lying in the direction of the Z-axis in a plane parallel to the Y-Z plane. The X-intercept, the Y-intercept and the Z-intercept define the distances of the vertices of the elliptical model from an origin in the X, Y, Z coordinate system with the origin corresponding to the center of the orifice.

In this aspect of the method, the first flow velocity distribution is obtained through an array ultrasonic transducer, the center of the transducer being positioned on the X-axis and the scan direction thereof being parallel to the X-axis. The second flow velocity distribution is obtained through the array ultrasonic transducer when the scan direction is positioned to be parallel to the Y-axis in a plane parallel to the Y-Z plane. The third flow velocity distribution is obtained through the array ultrasonic transducer when the scan direction is positioned to be parallel to the Z-axis in a plane parallel to the Y-Z plane.

Another aspect of the present invention is a method for estimating the volume of flow across an orifice at a wall which separates a first chamber and a second chamber in an object. Assuming for reference that the orifice and the two chambers lie in an X, Y, Z coordinate system with an origin at the center of the orifice and with the X axis of the coordinate system lying parallel to the direction of the flow through the orifice (i.e., perpendicular to the plane of the orifice), the method comprises the step of transmitting an ultrasonic beam from a first position on an X-axis to the center of the orifice through the first chamber proximal to the orifice and measuring a first flow velocity distribution along the X-axis using the Doppler shift of ultrasonic waves reflected from particles in the flow. The method comprises the further step of transmitting an ultrasonic beam from a second position in the direction of the Y-axis to the center of the orifice through the first chamber and measuring a second flow velocity distribution in the Y-axis direction, again using the Doppler shift of ultrasonic waves reflected from the particles in the flow. The method includes the further step of transmitting an ultrasonic beam from a third position on the Z-axis toward the center of the orifice through the first chamber and measuring a third flow velocity distribution in the Z-axis direction using the Doppler shift of ultrasonic waves reflected from particles in the flow. The method further includes the steps of using the first, second and third flow velocity distributions to find first, second and third points, respectively, on the X-axis, the Y-axis and the Z-axis at which the respective flow velocity is a specified velocity; and describing an isovelocity surface by an elliptical model defined by points $\{X, Y, Z\}$ satisfying the relationship $$X^2/A^2 + Y^2/B^2 + Z^2/C^2 = 1,$$

where A is the distance between the first point and the origin along the X-axis, B is the distance between the second point and the origin along the Y-axis, and C is the distance between the third point and the origin along the Z-axis. The model is hemi-ellipsoidal in that only points on the surface on one side of the orifice (e.g., only points having a positive X value) are considered. Thereafter, the method includes the step of estimating the volume of the flow by calculating an area of the surface of the elliptical model in the first chamber and by multiplying the area by the specified velocity.

BRIEF DESCRIPTION OF THE DRAWING FIGURES

FIG. 7 is a graph comparing the calculated values of fluid flow obtained using the methods of the present invention and the prior art method with the fluid flow measured using empirical methods.

FIG. 9 is a partial block diagram similar to FIG. 4 showing the positioning of the ultrasonic probe along a second side wall of the two-chambered box to obtain a view perpendicular to the view of FIG. 5.

DETAILED DESCRIPTION OF THE PREFERRED EMBODIMENT

Figure 1:
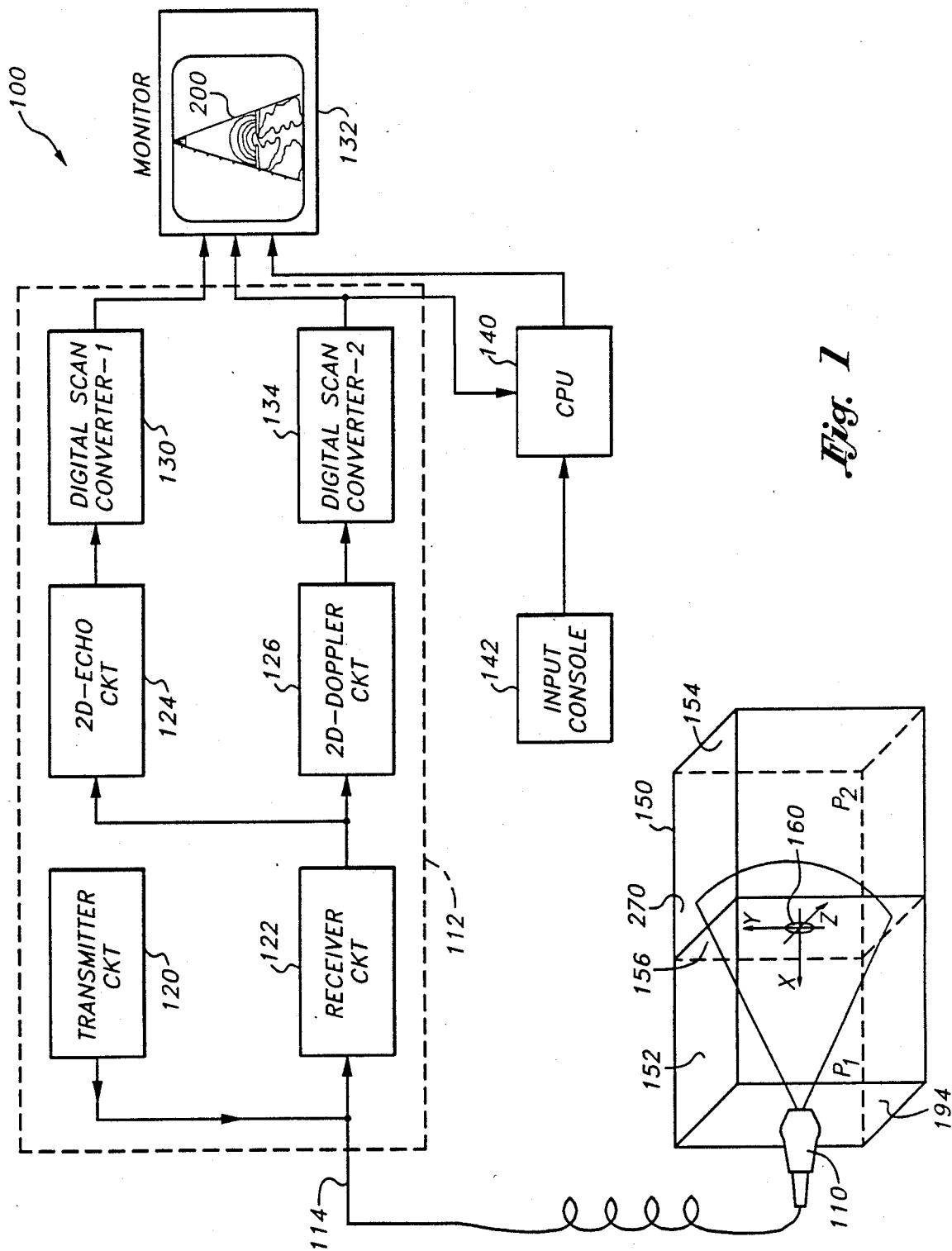
FIG. 1 illustrates a partial block diagram of an exemplary color Doppler imaging system in an experimental setup that demonstrates the method of the present invention, showing the positioning of the ultrasonic probe proximal to the liquid flow through the orifice in a two-chambered box.

FIG. 1 illustrates a partial block diagram of an exemplary color Doppler imaging system 100 in an experimental setup that demonstrates the method of the present invention. The color Doppler imaging system 100 comprises a probe 110 which includes an ultrasonic transmitter which transmits ultrasonic signal pulses and a receiver that receives echoes of the ultrasonic signal pulses and converts the received echoes to an electrical representation of the received echoes.

The probe 110 is connected to an imaging system electronics subsystem 112 via a cable 114. The electronics subsystem 112 transmits control signals to the probe 110 to cause it to transmit the ultrasonic signals and receives electrical signals responsive to the received echoes from the probe 110 via the cable 114.

As illustrated, the electronics subsystem 112 of the imaging system 100 includes a transmitter circuit 120 that generates a drive signal for the ultrasonic transducer within the probe 110 at a selected frequency. For example, in one particular embodiment using the Hitachi EUB-151 system, the frequency of the transducer drive signal generated by the transmitter circuit 120 is approximately 5 MHz.

The electronics subsystem 112 further includes a receiver circuit 122 that receives the electrical signals from the probe 110 and pre-processes (e.g., amplifies and filters) the signals and provides the processed signals to a two-dimensional echo circuit (2D-ECHO CKT) 124 and a two-dimensional (2D) Doppler circuit (2D-DOPPLER CKT) 126 within the electronics subsystem 112. The two-dimensional echo circuit 124 operates to locate the position and acoustic reflective properties of features in the scanned object (e.g., the patient's heart) in accordance with the times of arrival and intensities of the echoes from the features. The two-dimensional Doppler circuit 126 generally operates to assign velocity values within a region of interest in the features located by the two-dimensional echo circuit 124.

The output of the two-dimensional echo circuit 124 is provided as an input to a first digital scan convertor circuit (DIGITAL SCAN CONVERTER-1) 130 which converts the location and intensity information generated by the two-dimensional echo circuit 124 into pixel information and stores the pixel information at a pixel memory location associated with the location of the feature in the scanned object. The pixel information is transmitted to a color display monitor 132 in synchronism with the horizontal and vertical scanning electronics of the color display monitor 132 so that the features of the image of the scanned object appear on the display monitor 132 in spatial relationships corresponding to the spatial relationship of the physical features in the scanned object.

Similarly, the two-dimensional Doppler circuit 124 provides velocity information as an output to a second digital scan convertor (DIGITAL SCAN CONVERTER-2) 134 which stores a representation (i.e., color) of the velocity information in a memory location associated with the location of each feature causing an echo of the ultrasonic signal. The second digital scan converter 134 causes the velocity representation to be output to the color display monitor 132 in synchronism with the horizontal and vertical scanning electronics of the color display monitor 132.

The output of the second digital scan converter 134 is further provided to a computer 140 which is controlled by an input console 142 which advantageously includes a keyboard and a mouse (not shown). The computer 140 is responsive to commands from the input console 142 and is further responsive to signals received from the second scan converter 134 to control the information displayed on the color display monitor 132. For example, the computer 140 determines which colors are used to represent particular velocities on the color display monitor 132.

For ease in understanding the principle of operation of the present invention, the operation will be explained in connection with an experimental setup in which a leak between two chambers of a patient's heart is represented by a two-chambered box 150 having a first chamber 152 and a second chamber 154 separated by a partition 156. An orifice 160 is formed within the partition 156 to allow fluid to flow between the two chambers 152, 154. The size of the orifice 160 can be varied to control the rate of the fluid flow through the orifice 160. For example, in one set of experiments, the size of the orifice 160 was varied from 3 millimeters to 16 millimeters.

For convenience, in the discussion to follow, the proximal entrance to the orifice 160 is considered to be at the center of an X, Y, Z coordinate system with the X-axis of the coordinate system passing through the center of the orifice 160 and being substantially perpendicular to the partition 156 and thus perpendicular to the plane of the orifice 160. The positive direction of the X-axis is shown as being against the flow of liquid through the orifice 160 (i.e., pointing proximally away from the orifice 160). The Y-axis and the Z-axis are mutually perpendicular to each other and perpendicular to the X-axis and lie in a Y-Z plane parallel to the partition 156. As will be apparent in the following discussion, the Y-Z plane lies proximal to the partition 156.

In the experimental setup described herein, the two chambers 152, 154 are filled with a liquid such as a solution of cornstarch in water to simulate a patient's blood. For example, in one particular experiment involving the present invention, an approximately 2% by volume solution of cornstarch was used and was calibrated to a viscosity of 3.1 Centipoise which is generally equivalent to the viscosity of blood.

Figure 2:
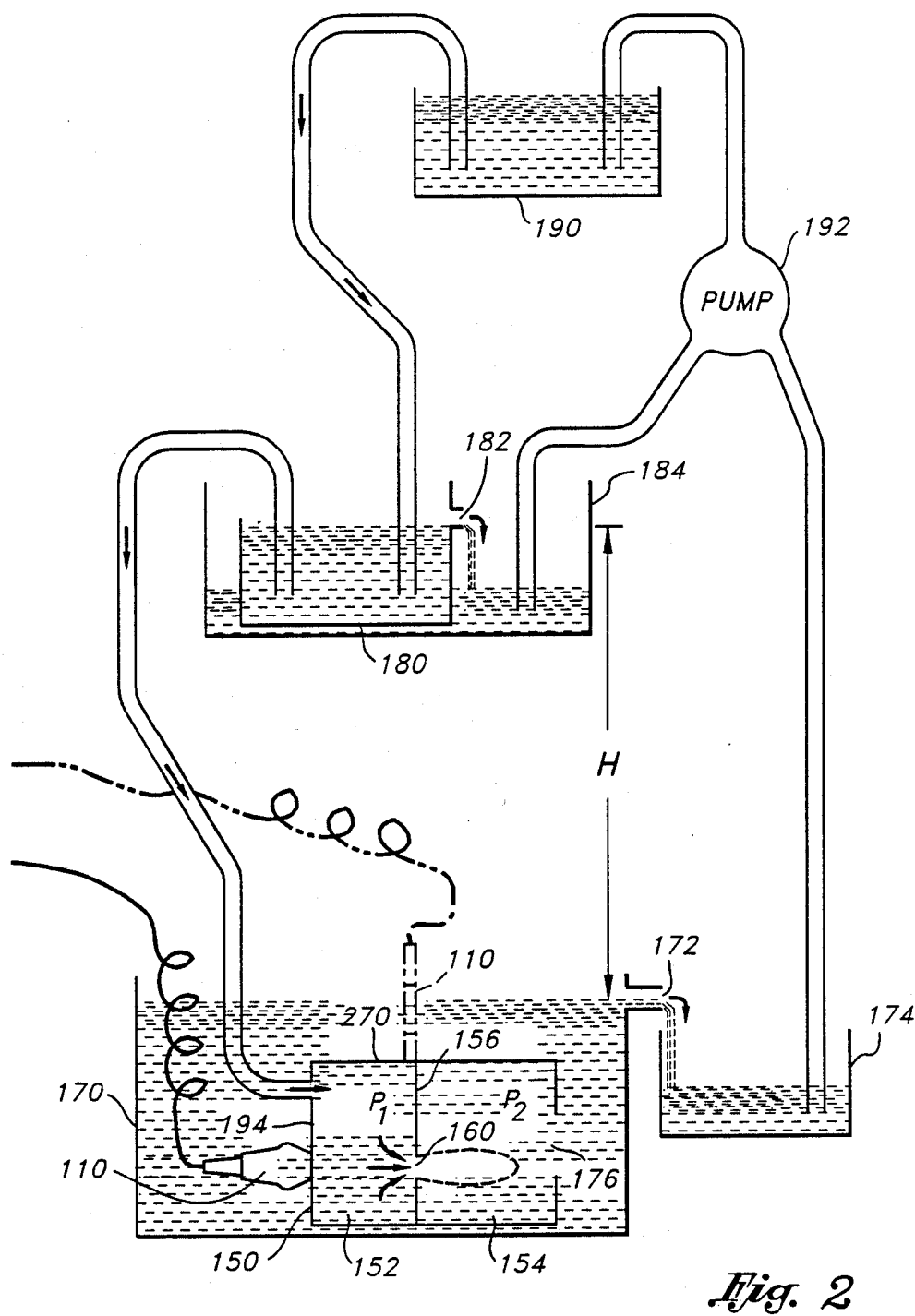
FIG. 2 illustrates an experimental setup in which a constant liquid flow is maintained through the orifice in a partition between the two chambers of the two-chambered box.

During a particular experiment, a first constant pressure P1 is maintained on the first chamber 152 and a second constant pressure P2 is maintained on the second chamber 154, the second constant pressure P2 being lower than the first constant pressure P1 so that the liquid will flow from the first chamber 152 to the second chamber 154 through the orifice 160 at a constant flow rate. For example, FIG. 2 illustrates a particular experimental setup in which the second constant pressure P2 is maintained by placing the box 150 in the bottom of a first tank 170 of the corn starch solution. The first tank 170 has an outlet 172 at a predetermined height above the bottom of the tank 170 that allows liquid to overflow into an overflow container 174. The second chamber 154 of the box 150 has an outlet 176 to the bottom of the first tank 170 so that the liquid in the second chamber 154 is at the same pressure as the liquid in the bottom of the first tank 170.

Similarly, the first constant pressure P1 is maintained by supplying the liquid as an input to the first chamber 152 from a second tank 180 having an outlet 182 at a constant predetermined height H above the outlet 172.

The liquid that overflows through the outlet 182 spills into an overflow container 184. The height differential H between the liquid levels in the first and second tanks 170, 180 provides the constant pressure differential between the first chamber 152 and the second chamber 154 of the box 150. In FIG. 2, the liquid flow between the second tank 180 and the first chamber 152 of the box 150 is maintained by siphoning action. By varying the height differential H between the outlets 172, 182 of the two tanks 170, 180 in the experiments (e.g., from 15 centimeters to 130 centimeters) in combination with variations in the orifice sizes, the constant flow rate for a particular experiment can be selected within a range of, for example, 0.5 to 18.7 liters per minute.

The second tank 180 is provided with liquid from a third tank 190 (e.g., by siphoning). The liquid that overflows from the first tank 170 into the overflow container 174 and the liquid that overflows from the second tank 180 into the overflow container 184 are provided as inputs to a pump 192 that constantly pumps the overflowing liquid back to the third tank 190 at a rate sufficient to maintain the height of the liquid in the second tank at the height of the outlet 182, thus maintaining the constant pressure differential.

It can be seen that in the experimental setup, the overflow from the first tank 170 through the outlet 172 corresponds to the flow of the liquid through the orifice 160 in the partition 156 between the two chambers 152, 154. The flow rate can thus be determined empirically by capturing the overflow liquid in a calibrated container over a predetermined amount of time and calculating the flow per unit time. The empirically determined flow rate can be compared with the flow rate determined by the method of the present invention and with the flow rate determined by other methods to demonstrate the accuracy of the present invention.

Returning to FIG. 1, the probe 110 is positioned on an outer wall 194 of the box 150 in alignment with the orifice 160 so that the ultrasonic signals generated by the probe 110 are directed toward the orifice 160. As illustrated, the probe 110 is positioned on the outer wall of the first chamber 152 so that the ultrasonic signals emitted by the probe 110 travel in the same direction as the flow of liquid through the orifice 160 from the first chamber 152 to the second chamber 154. The positioning of the probe 110 proximal to the orifice 160 with respect to the direction of flow of the liquid is an important aspect of the present invention in that it allows the flow rate to be accurately determined in accordance with the method of the present invention.

As schematically illustrated in FIG. 1, the ultrasonic signals transmitted by the probe 110 are transmitted in a fan-shaped beam that scans across the orifice 160 in a conventional manner to provide a two-dimensional dimensional representation of the liquid flow through the orifice 160. (For reference herein, the "scan direction" is the direction of the signals in the center of the fanshaped beam and is parallel to the X-axis using the coordinate system shown in FIG. 1.) The two-dimensional representation of the liquid flow is displayed on the display monitor 132 as a pie-shaped image 200 wherein the displayed colors within the pie-shaped image 200 represent the velocity of the liquid at a particular location in the scanned portion of the two chambers 152, 154. In other words, the image 200 represents a flow velocity distribution for the liquid passing through the orifice 160.

Figure 3:
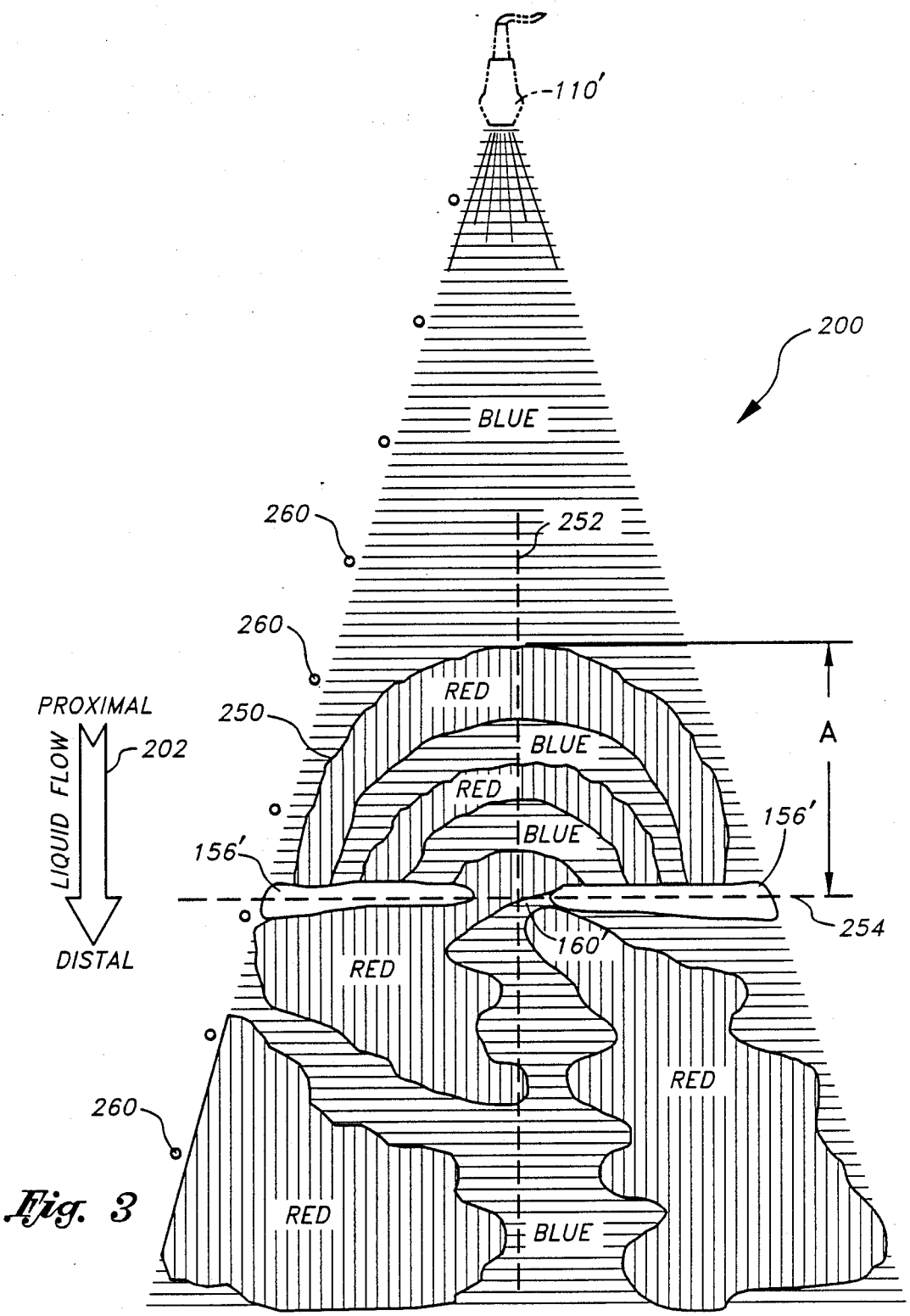
FIG. 3 illustrates a pie-shaped image segment such as will be displayed on the display monitor of FIG. 1 when the ultrasonic probe is positioned proximal to the orifice between the two chambers of the box.

FIG. 3 illustrates an enlarged view of one such pie-shaped display image 200 with the different colors of the display represented by different cross-hatching. For simplicity, only the red and blue velocity-indicating colors are shown. However, it should be understood that an actual display will include different shades of red and blue as well as other colors that represent liquid flow velocities and "variance" within the scanned portions of the two chambers 152, 154. In addition, a white color indicates the immobile portions of the partition 156 surrounding the orifice 160. The portions of the display representing the partition 156 and the orifice 160 are indicated at 156' and 160', respectively. For convenience, an arrow 202 is positioned alongside the display image 200 to indicate the proximal to distal direction of liquid flow through the orifice 160'. It should be understood that the arrow 202 does not appear on an actual display generated by the display monitor 132 (FIG. 1). Similarly, a phantom probe 110' is shown at the apex of the pie-shaped image 200 as a convenient indication of the position of the probe 110 with respect to the orifice 160. Again, the phantom probe 110' does not appear on the actual display on the display monitor 132.

As illustrated, the image 200 includes a plurality of generally semicircular alternating arcs of red and blue proximal to the orifice 160'. As previously discussed, the color in the display represents the direction and velocity of flow of the liquid, with the blue color, representing, for example, liquid flow away from the probe 110' (i.e., proximal to distal in the direction of the arrow 202). Because the blue color only represents a finite range of velocities in the proximal to distal direction (e.g., 0 to 27 centimeters per second), a phenomenon referred to as "aliasing" occurs when the velocity of the liquid exceeds the maximum magnitude of the range. When the velocity is greater than the aliasing velocity (e.g., greater than 27 centimeters per second), the velocity is displayed as a shade of red. Although the red color is intended to indicate liquid flow in the distal to proximal direction, a skilled operator understands that the liquid cannot abruptly change direction and will thus understand that aliasing has occurred and that the color Doppler imaging system is displaying velocities in the range from in excess of 27 centimeters per second to 54 centimeters per second, for example, in the same direction. When the range of velocities represented by the red color shades are exceeded (e.g., 54 centimeters per second), aliasing will again occur with an abrupt shift from shades of red to shades of blue. The aliasing may occur a number of times as the velocity of the liquid flow increases as the liquid moves closer to the orifice 160'.

The aliasing between the red and blue colors provides significant information related to the velocity of the liquid flow as the aliasing occurs at a known velocity determined by the range setting on the color Doppler imaging system. As discussed above, the range setting for the experiments described herein was adjusted so that the aliasing occurred at 27 centimeters per second, although it should be understood that other settings can be used.

It can be seen in FIG. 3 that the liquid flowing through the orifice 160' is represented by generally welldefined color areas proximal to the orifice 160', while, on the other hand, the liquid flow distal to the orifice 160' is disturbed flow as represented by complex color shapes (including variance). Although there have been attempts to determine liquid flow rate (i.e., volume per unit time) through an orifice by evaluating the velocities in the liquid flow distal to the orifice 160′, such attempts have generally not been very successful.

Bargiggia, et al., first suggested that the aliasing velocities in the liquid flow proximal to an orifice can be used to determine actual liquid flow through the orifice. Bargiggia, et al., suggested that the red/blue interface representing an aliasing velocity defines an isovelocity line (i.e., a line representing identical velocities). Bargiggia, et al., further suggested that the diameter of the generally semicircular isovelocity line can be considered to be the diameter of an isovelocity hemisphere having a surface that represents the locations relative to the orifice 160′ having liquid flow at the same common aliasing velocity. Since the surface area of the hemisphere can be readily calculated, then the flow through the orifice 160′ can be calculated by multiplying the surface area by the aliasing velocity.

Applicants herein have evaluated the Bargiggia, et al., hemispherical modeling method using the experimental setup described in FIGS. 1 and 2 and have determined that the Bargiggia, et al., method does not provide a sufficiently accurate determination of liquid flow rate when compared with the empirical measurements, particularly for non-circular orifices. On the other hand, Applicants have discovered a new method of determining liquid flow that compares well with the empirical flow determination described above.

DESCRIPTION OF THE METHOD OF THE PRESENT INVENTION

Unlike the Bargiggia, et al., method, the method of the present invention is based upon the recognition that the liquid flow through an orifice, such as the orifice 160 in FIGS. 1 and 2 is a complex flow that cannot be accurately represented by a hemispherical isovelocity surface. Rather, in the method of the present invention, an isovelocity surface is defined that more accurately represents the three-dimensional flow of liquid to and through the orifice 160.

The first step of the present method has been described above, and requires the measurement of the liquid flow in accordance with FIGS. 1 and 3. That is, the probe 110 is positioned proximal to the orifice 160 with the probe 110 aligned with the centerline of the orifice 160 and thus aligned with the axis of the flow through the orifice 160. The image 200 of FIG. 3 is generated as discussed above and is provided as an input to the next step of the method.

During the next step of the method, the image 200 taken along the axis of flow of the liquid through the orifice 160 is measured to determine the distance of a first isovelocity line 250 from the plane of the orifice 160′ along the axis of flow of the liquid. The axis of flow is represented by a phantom line 252 in FIG. 3 perpendicular to a line 254 in the plane of the orifice 160′. This first measured distance is saved and is referred to hereinafter as the distance A. The distance A will be used, as described hereinafter, to define an ellipsoidal isovelocity surface model.

It should be understood that the foregoing measurement of the distance A can be accomplished manually by working directly on the display monitor 132. In the preferred embodiment, the measurements are accomplished by transferring the data representing the image 200 to a second processing device, which is preferably a DEXTRA D-200 (not shown) image analysis computer, or the like. The data is transferred, for example, using high resolution video tape. The DEXTRA D-200 is particularly suited for making the measurements since the image from the video tape is displayed on a conventional high resolution computer monitor (not shown) and a mouse or other cursor control device can be used to define the starting and ending points for a length to be measured on the image 200. The DEXTRA D-200 includes software which automatically measures the distance between the starting and ending points and provides the measured distance as output data to the operator. Referring again to FIG. 3, it can be seen that the image 200 includes a plurality of reference markers 260 that are spaced apart from each other by a predetermined distance (e.g., 5 centimeters, or the like). The DEXTRA D-200 can be easily calibrated by using a pair of reference markers 260 as starting and ending points and providing the actual distance as input data to the DEXTRA D-200. Thereafter, the software within the DEXTRA D-200 can calculate a scale factor to be applied to subsequent measurements between two points on the stored image 200. The DEXTRA D-200 is a commercially available system used in echocardiography and other ultrasonic measurement applications for measuring portions of images produced by such ultrasonic measurements. The operation of the DEXTRA D-200 and similar equipment is well understood by those skilled in the art of ultrasonic measurements. In particularly preferred embodiments of the present invention, the functions of the DEXTRA D-200 can be incorporated into the computer 140 of FIG. 1 so that the measurements and flow volume calculations described hereinafter can be performed using the computer 140 and the associated input console 142.

Figure 4:
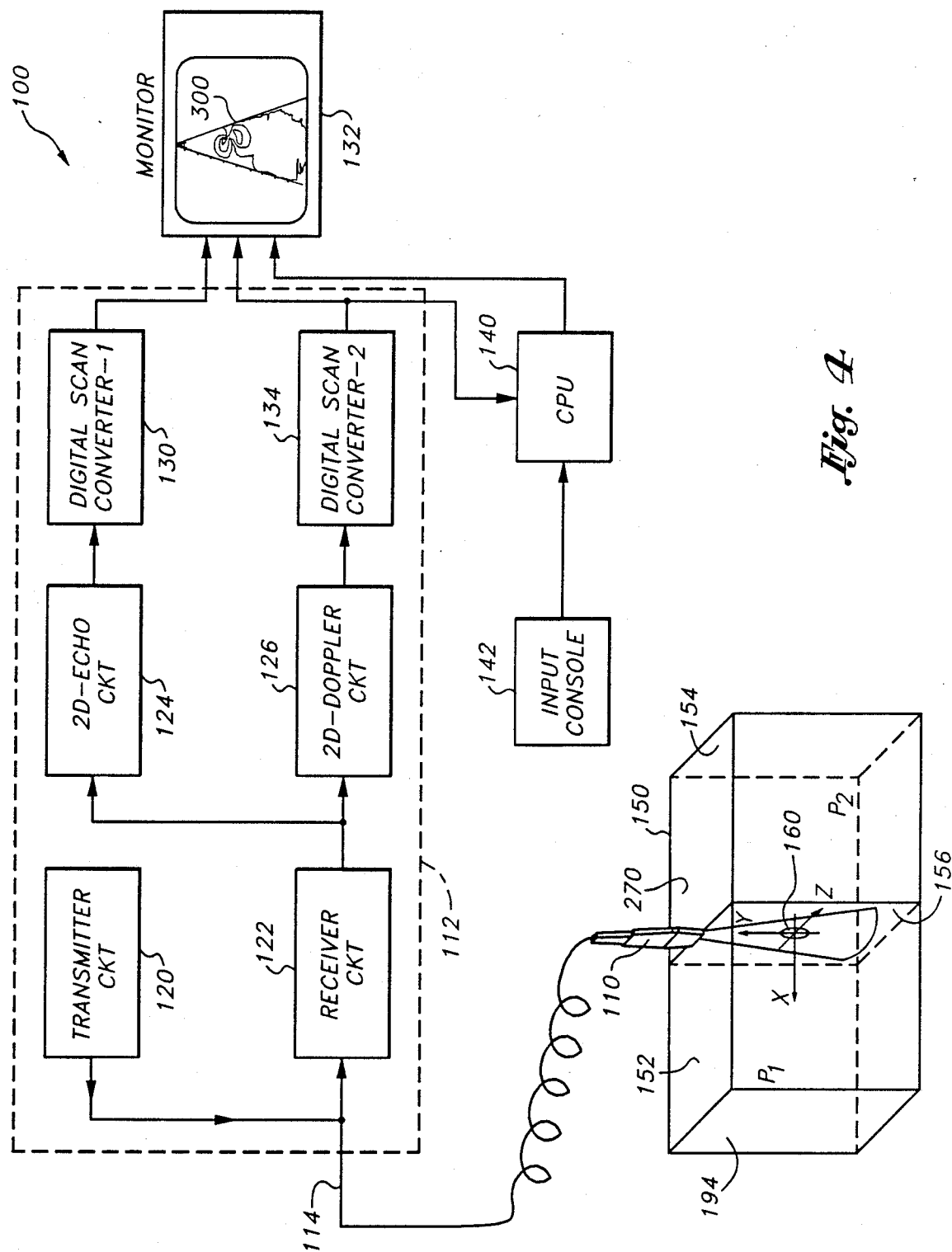
FIG. 4 is a partial block diagram similar to FIG. 1 showing the positioning of the ultrasonic probe along the side wall of the two-chambered box to obtain a view perpendicular to the view of FIG. 3.

After measuring the long axis distance A, the probe 110 is repositioned on a top wall 270 of the box 150 such that the ultrasonic signals are directed parallel to the plane of the partition 156 so that the ultrasonic signals are generally parallel to the partition 156, as illustrated in FIG. 4. Thus, the ultrasonic signals are radiated in a plane perpendicular to the flow of the liquid through the orifice 160. The probe 110 is positioned slightly proximal to the plane of the partition 156 so that the plane of the ultrasonic signal scan is slightly proximal to the partition 156 and thus detects the flow of liquid in radial directions toward the perimeter of the orifice 160 rather than axial as described above. Using the coordinate system shown in FIG. 4, the "scan direction" is parallel to the Y-axis in a plane parallel to the Y-Z plane (i.e., in a plane perpendicular to the X-axis).

Although Bargiggia, et al., assumed that the flow of the liquid through the orifice would be supplied along a hemisphere defined by an isovelocity surface, Applicants' experiments have shown that the liquid flowing along radial lines that are at substantial angles with respect to the axial flow through the orifice 160 (i.e., at substantial angles with respect to the axial line 252 of FIG. 3) does not flow as rapidly at a given distance from the orifice 160. Thus, for example, the liquid that flows generally parallel to the partition 156 until it reaches the orifice 160 and then turns to flow through the orifice will be travelling much slower at a given distance from the orifice 160 than liquid that is flowing straight through the orifice in a direction perpendicular to the partition 156. The ultrasonic scan in this step thus detects the velocity of the liquid in a direction parallel to the partition 156.

Figure 5:
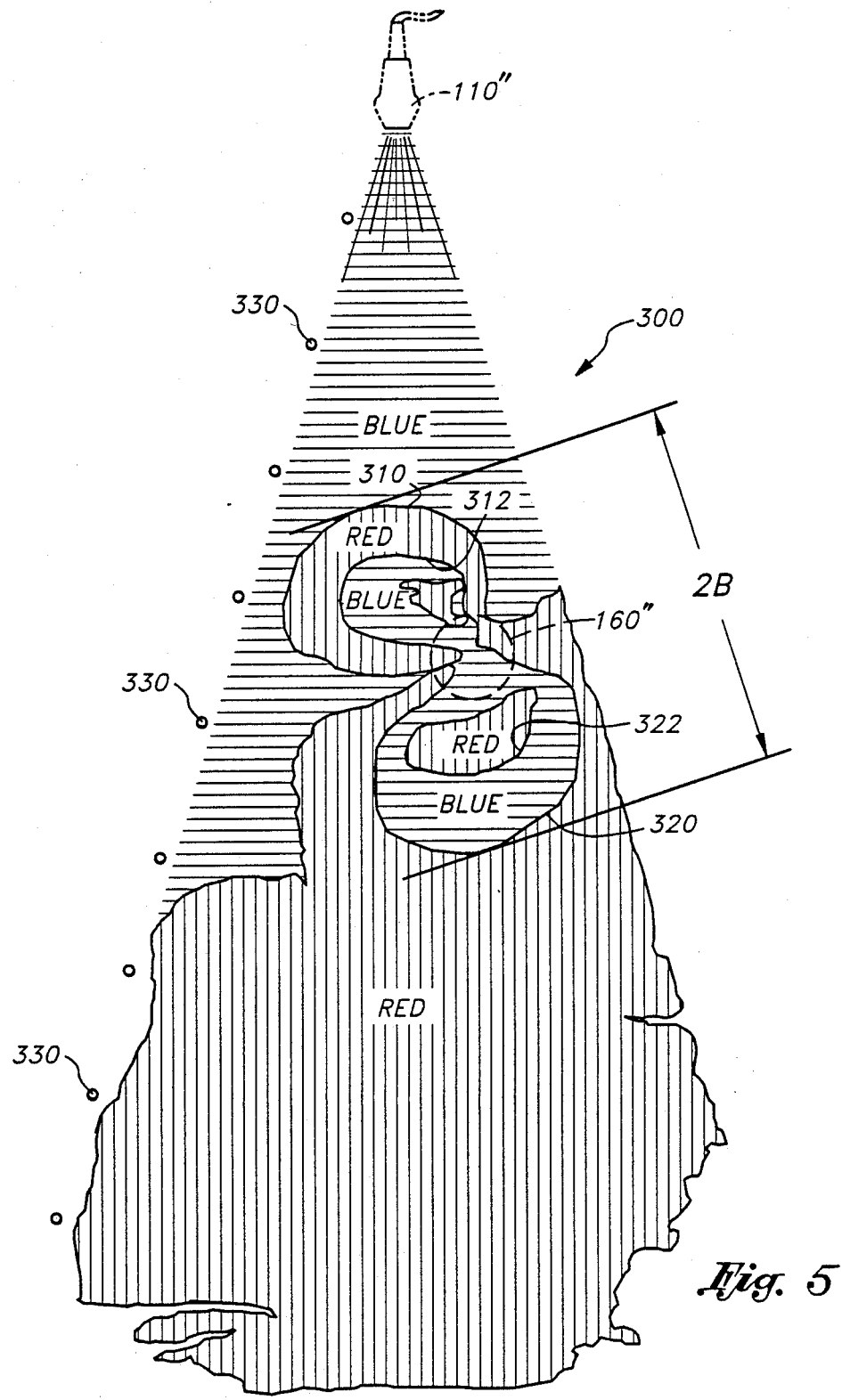
FIG. 5 illustrates a pie-shaped image segment such as will be displayed on the display monitor of FIG. 4 when the ultrasonic probe is positioned perpendicular to the flow through the orifice of the box.

An exemplary image 300 resulting from the measurement taken in accordance with the step illustrated in FIG. 4 is illustrated in FIG. 5. It can be seen that the image again comprises red and blue portions that respectively indicate fluid motion toward the probe 110 and fluid motion away from the probe 110. For reference, a phantom probe 110" is positioned at the top of the image 300 to show the source of the ultrasonic signals. As an additional reference, a phantom circle 160" is shown to represent the position of the orifice 160. Neither the probe 110" nor the orifice 160" appear on the actual image 300 produced by the color Doppler imaging system 100 of FIG. 1.

Again, the fluid motion in portions of the image 300 is of sufficient magnitude that the aliasing phenomenon occurs so that a red/blue interface is displayed to indicate that the fluid velocity exceeds the range represented by a particular color. For example, the top portion of the image 300 in FIG. 5 is generally blue to indicate that the fluid flow is away from the probe 110" toward the orifice 160". Similarly, the bottom portion of the image 300 is generally red to indicate that the fluid flow is generally toward the orifice 160" and the probe 110".

Near the center of the image 300 looking from the top downward, a blue/red interface 310 represents the first aliasing velocity caused by the increase in the velocity of the fluid as it nears the orifice 160". This first aliasing velocity has a known velocity that represents the maximum range set by the computer 140 in response to commands from the input console 142. As the fluid gets still closer to the orifice 160", the fluid velocity increases such that a second aliasing velocity occurs as illustrated by a red/blue interface line 312. In like manner, looking from the bottom of the image 300 upward, a red/blue interface 320 represents the first aliasing velocity of the fluid, and a blue/red interface 322 represents the second aliasing velocity of the fluid. It can be seen that the blue/red interface 310 and the red/blue interface 320 are disposed on opposite sides of the orifice 160" approximately in the center of the image 300.

It should be understood that the flow of the liquid into the circular orifice 160 in the physical embodiment of FIG. 4 is generally symmetrical about the orifice 160. In FIG. 5, the dumbbell shape of the red/blue and blue/red interfaces of the image 300 with respect to the orifice 160" result from the fact that the physical flow of the liquid in FIG. 4 represented by the portion of the image 300 to the right and to the left of the orifice 160" in FIG. 5 is generally perpendicular to the ultrasonic signals generated by the probe 110. Since the Doppler effect operates on motion to and away from the ultrasonic signals, as the flow becomes increasingly perpendicular to the ultrasonic signals, the displayed colors indicate decreasing flow rates although the actual flow rate is not decreasing. Thus, the displayed image 300 has a pinched-in appearance when viewed horizontally through the orifice 160".

Once the image 300 has been created as just described, the distance between the blue/red interface 310 and the red/blue interface 320 on the image 300 is measured. As discussed above, the measurement can be accomplished manually; however, the measurement is preferably performed using the DEXTRA D-200, or the like. The image 300 includes a plurality of calibration markers 330 for this purpose.

The distance between the blue/red interface 310 and the red/blue interface 320 is shown in FIG. 5 as a distance 2B, with one-half this distance (i.e., the distance between one of the interfaces 310, 320 and the center of the orifice 160") being shown as a short axis distance B.

Figure 6:
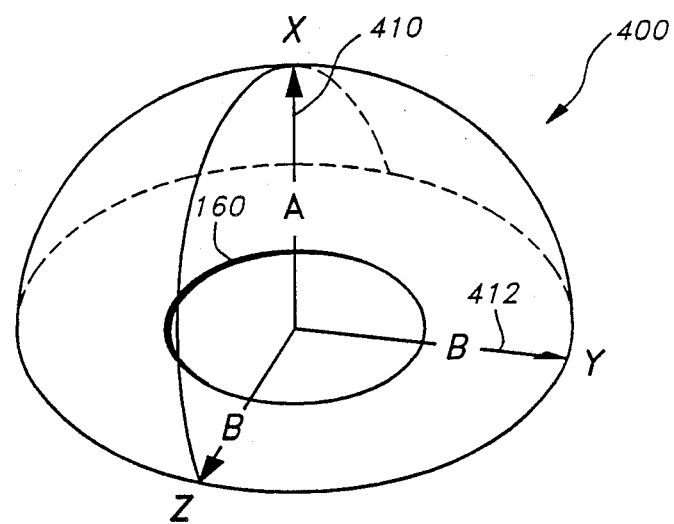
FIG. 6 illustrates a hemi-ellipsoidal model of the liquid flow through the orifice using distances measured from the image segments of FIGS. 3 and 5.
Figure 2:
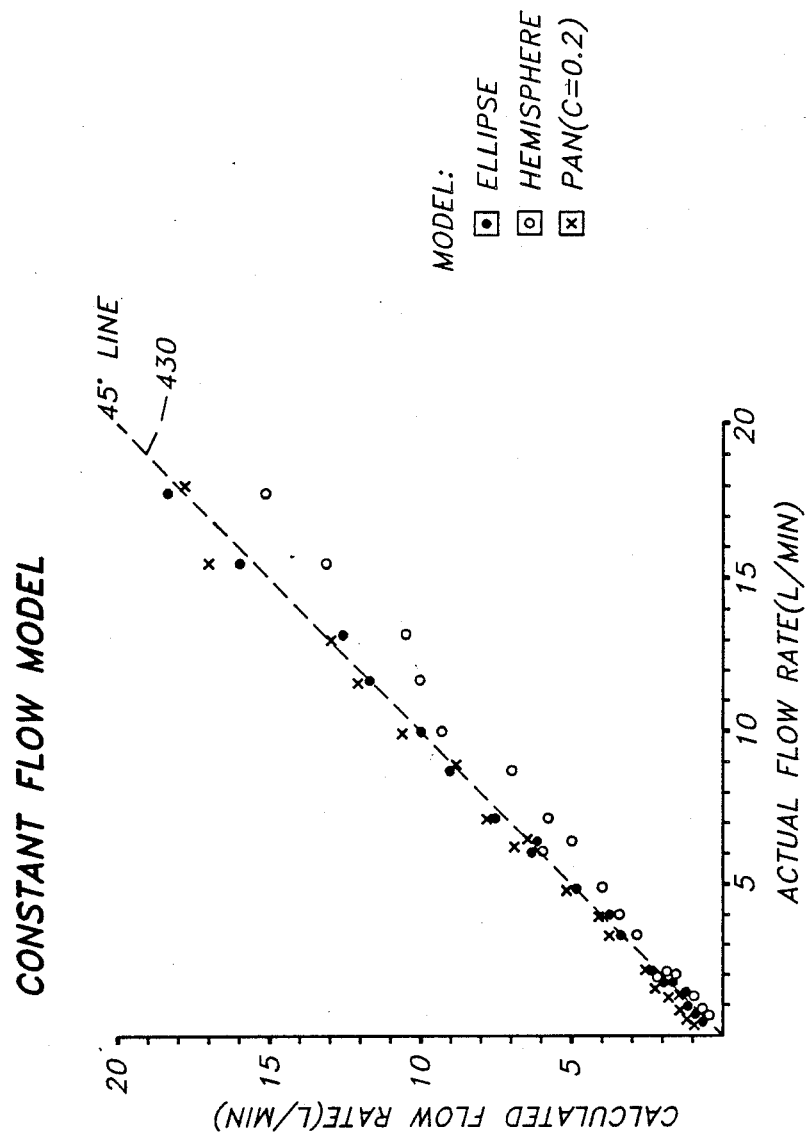

After measuring the long axis distance A and the short axis distance B, the method of the present invention, uses the two measured distances as the bases for an hemi-ellipsoidal model 400 of the liquid flow through the orifice 160 as illustrated in FIG. 6. It can be seen that the hemi-ellipsoidal model 400 has a first axis 410 that corresponds to the long axis distance A measured from the image 200 of FIG. 3 and a second axis 412 that corresponds to the short axis distance B measured from the image 300 of FIG. 5. The first axis 410 and the second axis 412 of the model 400 are positioned to intersect at the center of the orifice 160. The elliptical model 400 is a surface of revolution of an ellipse about an X axis corresponding to the first axis 410, the ellipse being defined as:

$$X^2/A^2 + Y^2/B^2 = 1 \quad (1)$$

The X-axis of revolution is perpendicular to the partition 156 and penetrates the center of the orifice 160. The Y-axis corresponds to the second axis 412. It can be seen that when the center of the orifice 160 is considered to be the origin of an X, Y, Z coordinate system, the distance A corresponds to the X-intercept (i.e., the intersection of the ellipsoidal surface with the X-axis) and the distance B corresponds to the Y-intercept (i.e., the intersection of the ellipsoidal surface with the Y-axis). The rotation of the ellipse around the X-axis produces an ellipsoid having a surface defined by $$X^2/A^2 + Y^2/B^2 + Z^2/B^2 = 1 \quad (2)$$

The Equation (2) is for the entire surface of the ellipsoid; however, the model is referred to herein as the "hemi-ellipsoidal" model since only the surface area proximal to the orifice is calculated. In the Equation (2), the distance B is the same for both the Y-axis and the Z-axis for this model.

In the experiments, the short axis distance B was greater than the long axis distance A. The proximal isovelocity surface area (PISA) is calculated from the long axis distance A and the short axis distance B in accordance with the following equation:

$$S = \pi B^2 + \frac{\pi B A^2}{\sqrt{B^2 - A^2}} \ln\left(\frac{B + \sqrt{B^2 - A^2}}{A}\right) \quad (3)$$

where A is the long axis distance between the center of the orifice 160' and red-blue color interface 250 on the long axis view image 200 of FIG. 3; and where B is the short axis distance between the center of the orifice 160" and the red-blue interface 310 on the short axis view image 300 of FIG. 5.

In the event that the short axis distance B is less than the long axis distance A, then the proximal isovelocity surface area S can be calculated in accordance with the following equation:

$$S = 2\pi(B^2 + AB(\text{Arc sin } \alpha)/\alpha) \quad (4)$$

where:

$$\alpha = \frac{\sqrt{A^2 - B^2}}{A},$$

After calculating the proximal isovelocity surface area in accordance with the Equation (3) or the Equation (4), the flow rate of the liquid through the orifice 160 is calculated by multiplying the surface area by the aliasing isovelocity at the red/blue interfaces:

$$FR = PISA \times V \qquad (5)$$

where FR is the flow rate in cubic centimeters per second (cm$^3$/sec), PISA is surface area in square centimeters (cm$^2$), and V is the aliasing isovelocity in centimeters per second (cm/sec).

By choosing the outermost red/blue or blue/red interfaces, the aliasing velocity is the first aliasing velocity which is the maximum range for the color representations. For example, in the exemplary experiment described herein, the aliasing velocity has a magnitude of 27 cm/sec. Thus, V in the Equation (5) would be 27 cm/sec for this example.

The above-described calculation of the flow rate using the hemi-ellipsoidal model of the isovelocity surface has been compared with the actual flow rates determined by measuring the constant flow for a known amount of time (i.e., by capturing the overflow from the outlet 172 of the first tank 170). The results of the comparison for a circular orifice 160 are illustrated in FIG. 7 which is a graph of calculated flow rate (vertical axis) versus actual measured flow rate (horizontal axis). Both axes are calibrated in liters per minute. The ideal correlation between the calculated flow rate and the empirically measured flow rate is illustrated by a 45° dashed line 430 from the origin of the graph. The actual calculated flow rates using the hemi-ellipsoidal model of the present invention are indicated by small closed circles on the graph for various actual flow rates. It can be seen that the calculated flow rates compare quite well with the empirically measured flow rates. The fit of the calculated values about a regression line can be expressed mathematically in the format y=mx+b, where y is the calculated flow rate, x is the actual empirically measured flow rate, b is the y-intercept of the regression line and m is the slope of the regression line. The slope m of the relationship between the calculated and measured values was 0.97 compared with an ideal slope of 1.0. The correlation coefficient r was 0.998, and the standard error of the estimate (SEE) was 0.14 liters per minute.

A set of open circles on the graph in FIG. 7 illustrate the calculations using the hemispherical model of Bargiggia, et al. The fit of the hemispherical model can be expressed as r=0.995, slope=0.79 and SEE=0.18 liters per minute. It can be seen that, for a circular orifice 160, the Bargiggia, et al., hemispherical model generally underestimates the actual flow rate by an average of approximately 18% of the actual flow rate and is thus less accurate than the hemi-ellipsoidal model of the present invention which underestimates the actual flow rate by an average of approximately 5%.

Figure 8:
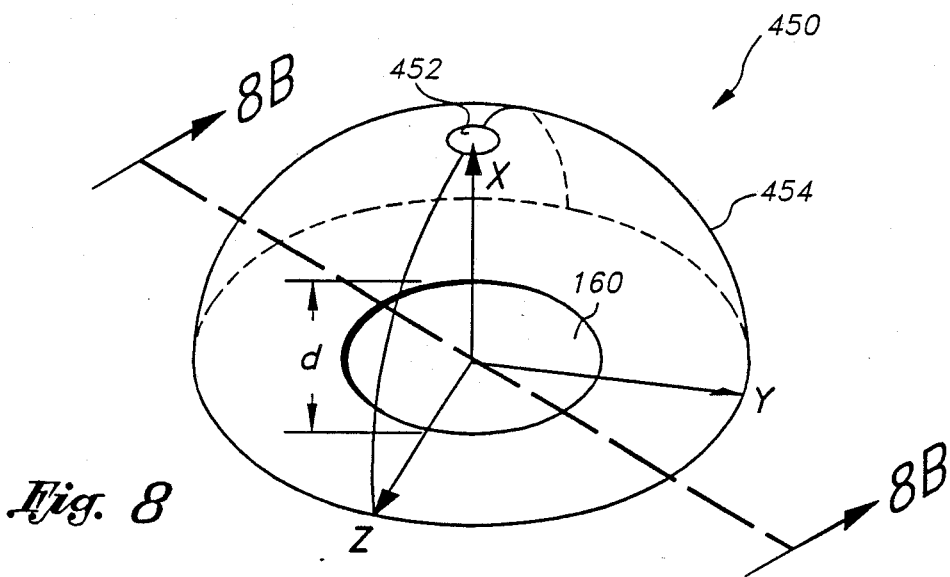
FIG. 8 illustrates a pan-shaped model of the liquid flow through the orifice using the distances measured from the image segments of FIGS. 3 and 5.
Figure 8B:
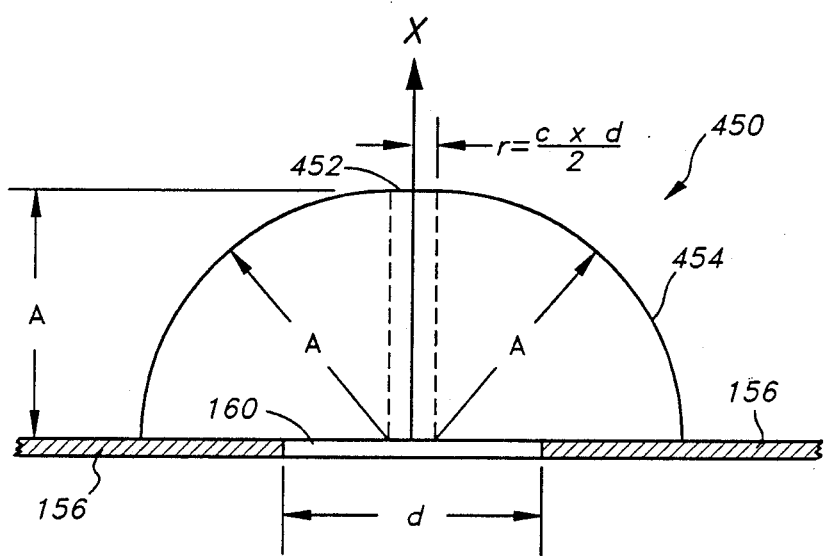
FIG. 8B is an elevational view of the pan-shaped model of FIG. 8 taken along the lines 8B—8B to provide additional details regarding the particular shape of the pan-shaped model.

An alternative model to the hemi-ellipsoidal model described above is a so-called "pan" model. The pan model recognizes that for a sufficiently large orifice, the flow substantially parallel to the axis comprises a column of liquid rather than a single axial line. Thus, the pan model comprises a pan-shaped surface 450 as illustrated in FIGS. 8 and 8B. It can be seen that the pan-shaped surface 450 comprises a flat circular portion 452 that is substantially parallel to the plane of the orifice 160. The flat portion 452 is symmetrically disposed about the X-axis and has a radius r. The edges of the flat portion 452 are contiguous with a generally radial peripheral surface 454 best illustrated in the elevational view of FIG. 8B. As illustrated, the peripheral surface 454 is formed by rotating a 90° segment of a circle of radius A (measured from the image 200 of FIG. 3) about the X-axis. The 90° segment extends from the Y-Z plane (i.e., the plane parallel to the partition 156 in which the orifice 160 is formed) to the edge of the flat portion 450. The origin of the radius defining the 90° segment is not on the X-axis (i.e., the origin of the radius of length A is not at the center of the orifice 160). Instead, the origin of the radius of the 90° segment is offset from the X-axis by the radius r of the flat portion 452. Thus, the rotation of the 90° segment about the X-axis does not define a hemisphere. Rather, it defines the boundaries of a pan-shaped or bowl-shaped surface, as shown.

The following equation is used to calculate the proximal isovelocity surface area using an assumption of a pan-shaped surface model:

$$PISA = \frac{\pi^2 cdA}{2} + 2\pi A^2 + \pi \left\{\frac{cd}{2}\right\}^2 \qquad (6)$$

where A is the distance between the orifice and red-blue color interface in the long axis view image 200 of FIG. 3; c is a coefficient; and d is the orifice diameter. The coefficient c is an empirical number for the pan-shaped model and is the ratio of the model's top flat circle diameter (i.e., 2r) to the actual orifice diameter d (i.e., 2r=c×d). The coefficient c was selected to provide the best fit of the calculated volume flow rate using the pan-shaped model to the actual volume flow rate. In experiments using the pan-shaped model, a coefficient c of 0.2 has been found to provide a sufficiently accurate approximation of the fluid flow through the orifice 160.

It should be noted that the pan-shaped model only requires that the A dimension taken from the image 200 in FIG. 3 be known. Thus, the pan-shaped model can be derived from a single image rather than the two orthogonal images. However, the pan-shaped model requires knowledge of the orifice diameter which may not be readily available in many clinical situations.

Referring again to FIG. 7, a set of x's represent the calculations of fluid flow using the pan model of FIGS. 8 and 8B. It can be seen that the pan model provides a close fit to the ideal 45° line of the graph. The fit of the pan model can be expressed as r=0.997, slope=0.98, and SEE=0.16 L/min which compares favorably with the ellipsoidal model. Thus, the pan-shaped model provides a good fit for applications where the size of the orifice is known.

The hemi-ellipsoidal model of FIG. 6 can also be used with non-circular orifices, such as ellipsoidal orifices. The above-described hemi-ellipsoidal model obtained by taking a long-axis measurement and a single short-axis measurement provides a better correlation with actual volume flow than the hemispherical method of Bargiggia, et al. For additional accuracy, a second short-axis measurement can be taken as illustrated in FIG. 9. The second short-axis measurement is taken in the same plane as the first short-axis measurement but is taken along an axis substantially perpendicular to the axis of the first short-axis measurement with the probe 110 positioned on a side wall 460 perpendicular to the top wall 270. Using the coordinate system shown in FIG. 9, the "scan direction" is parallel to the Z-axis in a plane parallel to the Y-Z plane (i.e., in a plane perpendicular to the X-axis).

Figure 10:
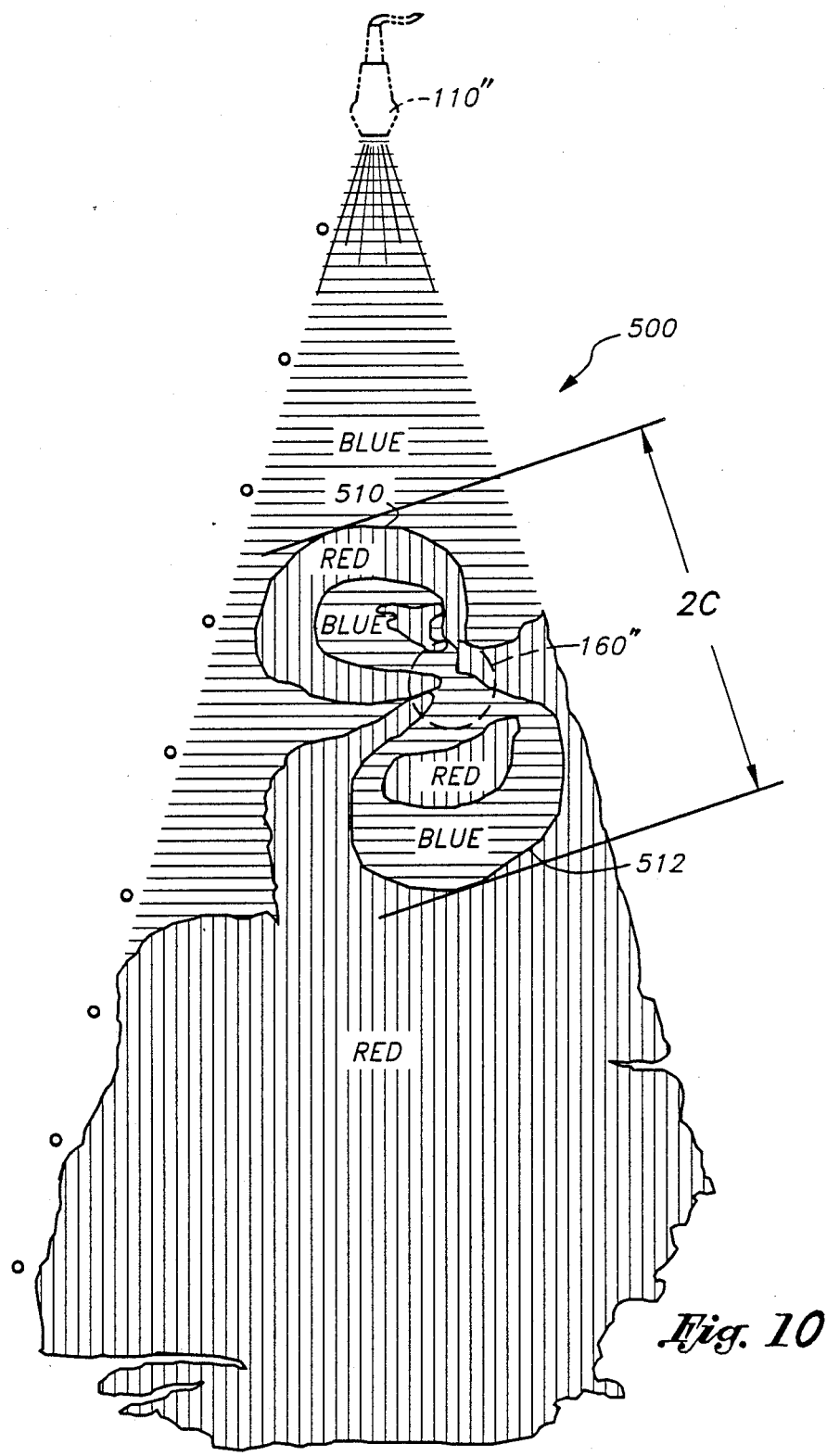
FIG. 10 illustrates a second pie-shaped image segment such as will be displayed on the display monitor of FIG. 9.

FIG. 10 illustrates an image 500 produced by the second short-axis view. As illustrated, the image 500 is similar to the image 300 produced by the first short-axis view. A measurement is taken between a blue/red interface 510 and a red/blue interface 512 to obtain a distance 2C which is twice the distance C from one of the interfaces 510, 512 to the center of the orifice, again represented as a phantom orifice 160''.

Figure 11:
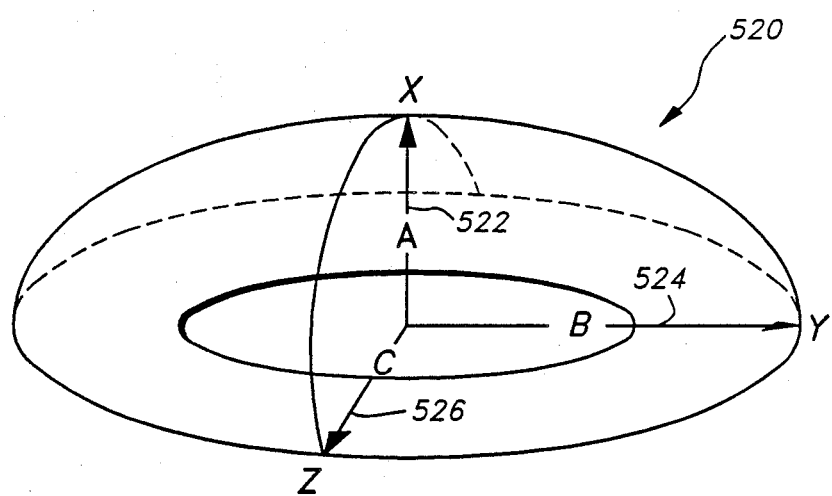
FIG. 11 illustrates a hemi-ellipsoidal model having axial dimensions taken from the images in FIGS. 3, 5 and 10.

FIG. 11 illustrates a hemi-ellipsoidal model 520 having a first axis 522, having a length A from the origin along the X-axis that corresponds to the distance A measured from the image 200 of FIG. 3; having a second axis 524, having a length B along the Y-axis from the origin that corresponds to the distance B measured from the image 300 of FIG. 5; and having a third axis 526, having a length C along the Z-axis from the origin that corresponds to the distance C measured from the image 500 of FIG. 10. The hemi-ellipsoidal model of FIG. 11 represents a surface that comprises the points $\{X, Y, Z\}$ that satisfy the equation:

$$X^2/A^2 + Y^2/B^2 + Z^2/C^2 = 1 \tag{7}$$

As before, only those points where X is greater than or equal to zero are considered as part of the hemi-ellipsoidal surface model 520.

The surface of the hemi-ellipsoidal model 520 is an isovelocity surface representing the locations in the images 200, 300 and 500 where the velocities are equal to the aliasing velocity (e.g., 27 centimeters per second). The surface area of the hemi-ellipsoidal model 520 can be calculated as follows:

$$S = \pi BC \left( \frac{A^2}{BC} + \alpha \int_0^{\phi_0} \sqrt{1 - k^2 \sin^2 \phi} \, d\phi + \frac{1-\alpha^2}{\alpha} \int_0^{\phi_0} \frac{d\phi}{\sqrt{1 - k^2 \sin^2 \phi}} \right) \tag{8}$$

where:

$$\alpha = \sqrt{1 - \frac{A^2}{C^2}},$$

where:

$$\beta = \sqrt{1 - \frac{A^2}{B^2}},$$

where:

$$k = \frac{\beta}{\alpha} = \sqrt{1 - \frac{A^2}{B^2}} / \sqrt{1 - \frac{A^2}{C^2}},$$

and where:

$$\phi_0 = \text{Arc sin} \sqrt{1 - \frac{A^2}{C^2}}$$

Figure 12:
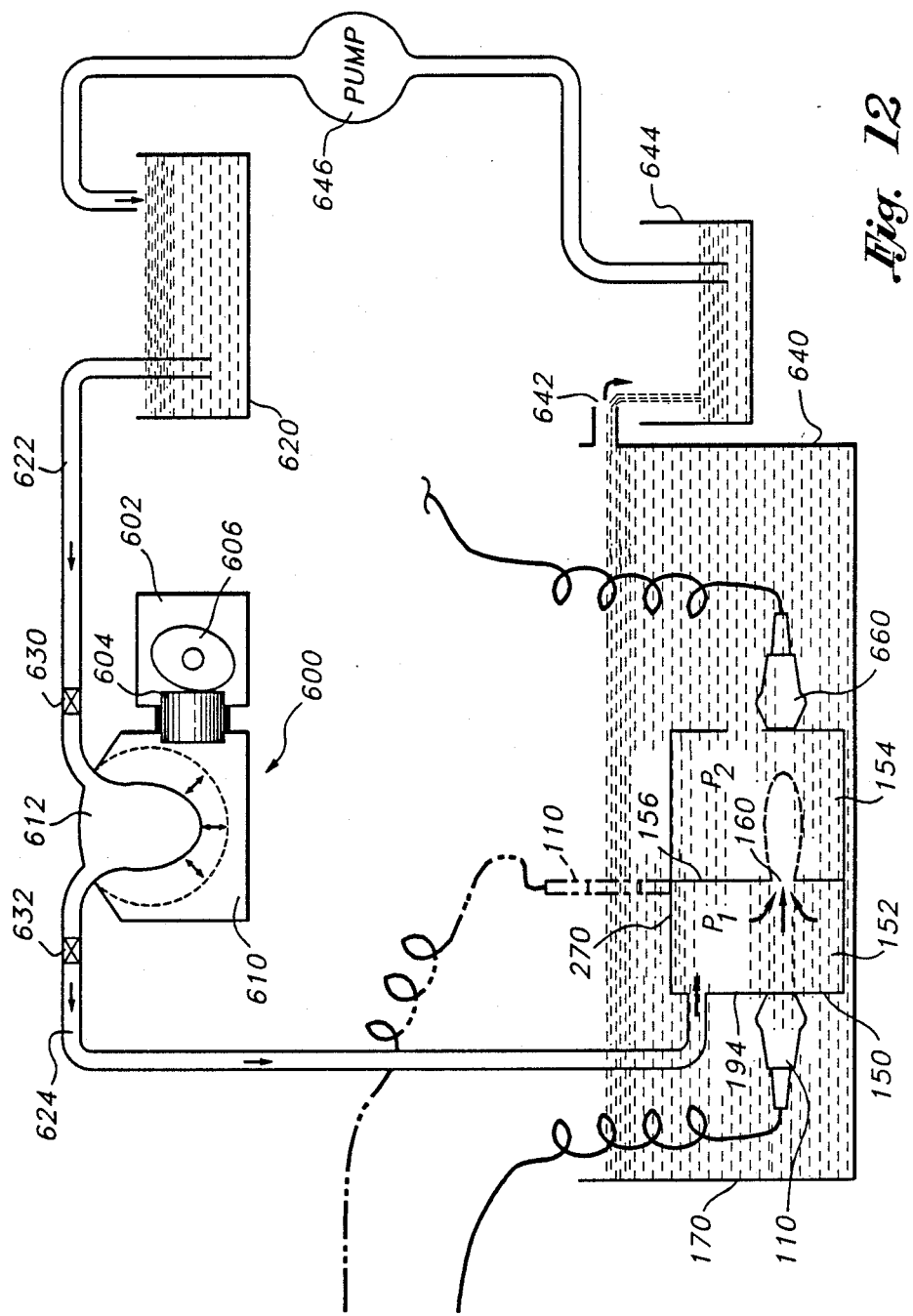
FIG. 12 illustrates an experimental setup wherein the flow through the orifice in the partition between the two chambers of the box is generated by a pump so that the flow occurs in predetermined pulses to simulate the cardiac action of a patient.

Although described above with respect to a constant flow experiment, it should be understood that the present invention also provides sufficiently accurate results when the liquid has pulsatile flow characteristics through the orifice 160. FIG. 12 illustrates an experimental setup wherein the flow through the orifice 160 in the partition 156 is generated by a pump 600 so that the flow occurs in predetermined pulses to simulate the cardiac action of a patient. The pump 600 comprises a motor 602 that drives a piston 604 in a reciprocating manner. For example, the piston 604 can be driven against the force of a spring (not shown) by a cam 606 having a camming surface that can be selected to simulate the variations in pressure during a cardiac cycle. The piston 604 pushes against a liquid in a chamber 610 to periodically increase and decrease the pressure of the liquid. A bladder 612 is suspended in the liquid in the chamber 610. The bladder 612 is connected to a supply tank 620 via an inlet tube 622 and is connected to the above-described box 150 via an outlet tube 624. The supply tank 620 holds a solution of cornstarch in water, as described above. A first one-way valve 630 is included in the inlet tube 622 so that liquid can flow only in the direction from the supply tank 620 to the bladder 612, and a second one-way valve 632 is included in the outlet tube 624 so that liquid can flow only in the direction from the bladder 612 to the box 150. The increases and decreases in the pressure in the chamber 610 are applied to the bladder 612 to cause the bladder 612 to draw liquid from the supply tank 620 and force liquid into the first chamber 152 of the box 150, thus causing pulsatile flow of liquid through the orifice 160 in the partition 156.

The box 150 is submerged in a second tank 640 having an outlet 642 to maintain a constant liquid level in the second tank 640, thus providing a constant pressure P2 in the second chamber 154 of the box 150. The overflow from the outlet 642 is captured in an overflow tank 644, as before. A second constant flow pump 646 is advantageously included to pump the liquid back to the supply tank 620 to allow the experiment to continue for extended time durations. Alternatively, the overflow can be measured over a predetermined number of pump cycles to empirically determine the average flow volume per pump cycle (i.e., the flow per "beat" of the simulated heart).

As illustrated in FIG. 12, the probe 110 is first positioned on the outer wall 194 of the box 150 to measure the flow in the long axis view and create an image similar to the image 200 of FIG. 3, and then positioned on the top wall 270, as illustrated by a second probe 110 in phantom in FIG. 12, to create an image similar to the image 300 of FIG. 5. For an elliptical orifice, the additional short axis view is also taken in accordance with FIG. 9 and the image representing the maximum velocity is selected.

Since the flow velocity changes throughout each pump cycle, it is necessary to evaluate each frame of the images 200, 300 (and 500 if using the model of FIG. 11) to select the respective frames that represent the peak velocity (i.e., the frames which have the first blue/red interface furthest from the orifice). The DEXTRA D-200 image analysis computer, described above, advantageously includes software to allow an operator to step through each image frame and select the appropriate image, either visually or through measurement of the distances A and B as described above. After measuring the images, a proximal isovelocity surface area (PISA) model is constructed as described above.

The stroke volume is calculated by first assuming that the proximal isovelocity surface area increases from 0 to its maximum area and then decreases to 0 in direct proportion to the change in velocity measured using a continuous wave Doppler recording in the liquid jet distal to the orifice 160, as indicated by the position of a probe 660 in FIG. 12. As is well known in the art, continuous wave Doppler techniques can accurately record the velocities encountered in echocardiography without encountering the aliasing phenomenon described above. Thus, the recording of the distal jet will provide a direct reading of the velocity of the flow through the center of the orifice 160. By measuring this velocity over time using the continuous wave Doppler, a flow velocity integral (FVI) in centimeters (i.e., the area under the flow velocity curve) can be calculated as well as the peak flow velocity (PFV) in centimeters per second through the orifice 160. Thereafter, the flow velocity integral and the peak flow velocity measured using continuous wave Doppler, along with the proximal isovelocity surface area and the isovelocity measured using the multi-gate pulsed wave color Doppler, can be combined to calculate the stroke volume (SV) as follows:

$$SV = PISA \times V \times (FVI/PFV) \qquad (9)$$

The flow rate (FR) can then be calculated as follows:

$$FR = SV \times HR \qquad (10)$$

where HR is the heart rate, which, in the experimental setup, is the rate at which the piston 604 in the pump 600 is cycled.

Figure 13:
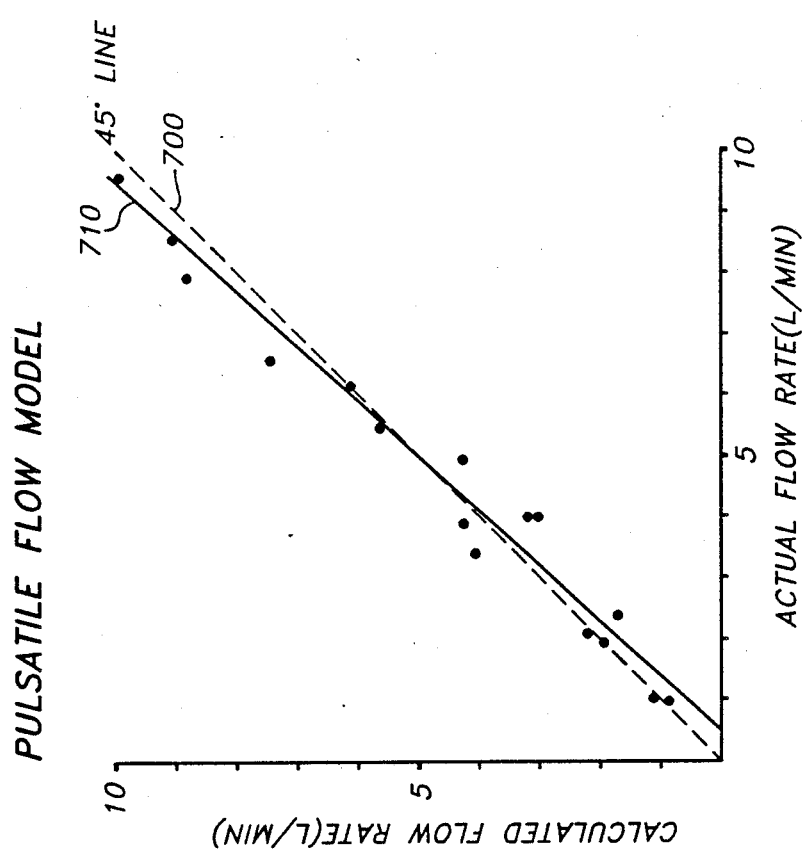
FIG. 13 is a graph comparing the calculated flow from the experimental setup of FIG. 12 with the empirically measured results.

The results of the experiments with the pulsatile model are illustrated by a graph in FIG. 13 wherein a dashed line 700 at a 45° angle to the origin represents the ideal relationship between the flow rate calculated in accordance with this aspect of the present invention (the vertical axis) and the empirically measured actual flow rate (the horizontal axis). A set of closed circles represent the calculated flow rates corresponding to the empirically measured actual flow rates. It can be seen that a best fit line 710 constructed through the calculated values is different from the line 700 but sufficiently close to the line 700 to show that the present invention can be used to provide non-invasive measurements of pulsatile liquid flow. It has been found that over a range of jet velocities at the orifice 160 from 2.6 meters per second to 7.7 meters per second, and flow rates ranging from 1.0 liters per minute to 10.3 liters per minute, the calculated flow rates using the proximal isovelocity surface area method and the elliptical model of the present invention demonstrates excellent correlation with the actual flow rate (r=0.985, slope=1.09 and SEE=0.25 liters per minute), where r, slope and SEE are defined as before.

It can be seen from the foregoing that the hemi-ellipsoidal models of the present invention in combination with a color Doppler imaging system provide excellent correlation in the measurement of constant flow and pulsatile flow of liquids compared to empirical measurements of the same flows.

Although described above in connection with particular embodiments of the present invention, it should be understood the descriptions of the embodiments are illustrative of the invention and are not intended to be limiting. Various modifications and applications may occur to those skilled in the art without departing from the true spirit and scope of the invention as defined in the appended claims.

What is claimed is:

1. A method for determining a volume of flow through an orifice at a wall which separates a first chamber and a second chamber in an object, comprising the steps of:

transmitting ultrasonic beams to said first chamber from first and second locations proximal to said orifice and measuring at least first and second flow velocity distributions in said first chamber using the Doppler shift of ultrasonic waves reflected from particles in said flow;

defining an isovelocity surface on which a plurality of isovelocity points within said first and second flow velocity distributions indicate a specified velocity, said isovelocity surface defined by an elliptical model; and estimating said volume of flow by calculating the area of said surface of said elliptical model and by multiplying said area by said specified velocity.

2. The method as defined in claim 1, wherein said elliptical model is a surface of revolution in an X, Y, Z coordinate system of an ellipse defined by $$X^2/A^2 + Y^2/B^2 = 1,$$

the axis of said revolution being the X-axis which is perpendicular to said wall and penetrates the center of said orifice, and A and B are measured from said first and second flow velocity distributions.

3. The method as defined in claim 2, wherein said step of defining said model includes the steps of:

defining A as an X-intercept of said ellipse by locating a first point within said first flow velocity distribution at which said flow velocity is said specified velocity; and defining B as a Y-intercept of said ellipse by locating a second point within said second flow velocity distribution at which said flow velocity is said specified velocity.

4. The method as defined in claim 1, wherein said elliptical model is defined by $$X^2/A^2 + Y^2/B^2 + Z^2/C^2 = 1,$$

on an X, Y, Z coordinate system having an origin at the center of said orifice, said X-axis being coincident with the direction of flow through said orifice, and wherein said step of describing said model includes the steps of:

defining A as an X-intercept of said elliptical model in an X-Y plane using first flow distribution;

determining B as a Y-intercept in a Y-Z plane using said second flow distribution; and determining C as a Z-intercept in a Y-Z plane using a third flow velocity distribution.

5. The method as defined in claim 4, wherein:

said first flow velocity distribution is obtained by positioning an array ultrasonic transducer on said X-axis and scanning said flow in a plane parallel to said X-axis;

said second flow velocity distribution is obtained by positioning said array ultrasonic transducer in the direction of said Y-axis and scanning said flow in a plane parallel to said Y-Z plane; and said third flow velocity distribution is obtained by positioning said array ultrasonic transducer in the direction of said Z-axis and scanning said flow in a plane parallel to said Y-Z plane.

6. A method for estimating a volume of flow across an orifice at a wall which separates a first chamber and a second chamber in an object, comprising the steps of:

transmitting an ultrasonic beam from a first position proximal to said orifice toward the center of said orifice through said first chamber, and measuring a first flow velocity distribution along an X-axis using the Doppler shift of ultrasonic waves reflected from particles in said flow;

transmitting an ultrasonic beam from a second position on a Y-axis toward said center of said orifice through said first chamber, and measuring a second flow velocity distribution along said Y-axis using the Doppler shift of ultrasonic waves reflected from said particles, said Y-axis being in a plane proximal to said orifice and perpendicular to said X-axis;

transmitting an ultrasonic beam from a third position on a Z-axis toward said center of said orifice through said first chamber and measuring a third flow velocity distribution along said Z-axis using the Doppler shift of ultrasonic waves reflected from said particles, said Z-axis being in a plane proximal to said orifice and perpendicular to said X-axis;

locating points on each of said X-axis, said Y-axis and said Z-axis at which the flow velocity is a respective specified velocity within said first, second and third flow velocity distributions;

defining an isovelocity surface by an elliptical model in accordance with the definition $$X^2/A^2 + Y^2/B^2 + Z^2/C^2 = 1,$$

where, A is the distance between said first point and said origin, B is the distance between said second point and said origin, and C is the distance between said third point and said origin; and calculating an area of a surface of said elliptical model in said first chamber and multiplying said area by said specified velocity to obtain the volume of said flow.

7. A method for estimating a volume of flow across an orifice at a wall which separates a first chamber and a second chamber in an object, comprising the steps of:

transmitting an ultrasonic beam from a position proximal to said orifice toward the center of said orifice through said first chamber, and measuring a flow velocity distribution along an axis perpendicular to a plane parallel to said wall using the Doppler shift of ultrasonic waves reflected from particles in said flow;

locating a point on said axis at which the flow velocity is a specified velocity within said flow velocity distributions;

defining an isovelocity surface by a pan-shaped model in accordance with the definition $$PISA = \frac{\pi^2 cdA}{2} + 2\pi A^2 + \pi\left(\frac{cd}{2}\right)^2$$

where A is the distance between said point and said plane of said wall, d is the diameter of said orifice and c is a constant; and calculating an area of a surface of said pan-shaped model in said first chamber and multiplying said area by said specified velocity to obtain the volume of said flow.

* * * * *